(12) United States Patent
Kamerling et al.

(10) Patent No.: US 12,194,312 B2
(45) Date of Patent: *Jan. 14, 2025

(54) COMPUTER-IMPLEMENTED MEDICAL METHOD FOR RADIATION TREATMENT (RT) PLANNING FOR TREATING MULTIPLE BRAIN METASTASES OF A PATIENT

(71) Applicant: Brainlab AG, Munich (DE)

(72) Inventors: Cornelis Kamerling, Munich (DE); Stefan Schell, Munich (DE)

(73) Assignee: Brainlab AG, Munich (DE)

( * ) Notice: Subject to any disclaimer, the term of this patent is extended or adjusted under 35 U.S.C. 154(b) by 1066 days.

This patent is subject to a terminal disclaimer.

(21) Appl. No.: 17/252,052

(22) PCT Filed: Jul. 16, 2020

(86) PCT No.: PCT/EP2020/070131
§ 371 (c)(1),
(2) Date: Dec. 14, 2020

(87) PCT Pub. No.: WO2021/058161
PCT Pub. Date: Apr. 1, 2021

(65) Prior Publication Data
US 2021/0260405 A1    Aug. 26, 2021

(30) Foreign Application Priority Data
Sep. 27, 2019   (WO) ............... PCT/EP2019/076214

(51) Int. Cl.
*A61N 5/10* (2006.01)
*G16H 10/60* (2018.01)
(Continued)

(52) U.S. Cl.
CPC ......... *A61N 5/1031* (2013.01); *A61N 5/1047* (2013.01); *A61N 5/1082* (2013.01);
(Continued)

(58) Field of Classification Search
None
See application file for complete search history.

(56) References Cited

U.S. PATENT DOCUMENTS 11,583,699 B2 *  2/2023  Kamerling ........... A61N 5/1081
2009/0041200 A1  2/2009  Lu et al.
(Continued)

FOREIGN PATENT DOCUMENTS

EP      3549636 A1 *  10/2019  ........... A61N 5/1031
WO   WO-2012099747 A2 *  7/2012  ............. A61B 5/055
(Continued)

OTHER PUBLICATIONS

Steven K.M. Lau et al, "Single-Isocenter Frameless Volumetric Modulated Arc Radiosurgery for Multiple Intracranial Metastases", Aug. 2015.
(Continued)

*Primary Examiner* — Carrie R Dorna
*Assistant Examiner* — Marc D. Honrath
(74) *Attorney, Agent, or Firm* — Tucker Ellis LLP

(57) ABSTRACT

The present application provides an initial, or first, packed arc setup to be compared with predefined arc setup constraints. These predefined arc setup constraints constrain at least one or more of the number of patient table angles per target volume, the number of times the gantry moves along one arc per table angle, the sum of gantry span per metastasis over all arcs, and the minimum table span. Based on the result of the comparison between the packed first arc setup with the predefined arc setup constraints, a second arc setup is automatically suggested. The automatically suggested second arc setup may then be compared with the first arc setup by calculating a score for both setups. Several iterations of such a method can be carried out based on the
(Continued)

comparison between an arc setup and the following, subsequent arc setup in the iteration.

26 Claims, 6 Drawing Sheets

(51) Int. Cl.
*G16H 20/40* (2018.01)
*G16H 40/40* (2018.01)
*G16H 40/63* (2018.01)
*G16H 50/20* (2018.01)
*G16H 50/30* (2018.01)
*G16H 50/70* (2018.01)
*G16H 70/20* (2018.01)

(52) U.S. Cl.
CPC ............. *G16H 10/60* (2018.01); *G16H 20/40* (2018.01); *G16H 40/40* (2018.01); *G16H 40/63* (2018.01); *G16H 50/20* (2018.01); *G16H 50/30* (2018.01); *G16H 50/70* (2018.01); *G16H 70/20* (2018.01)

(56) References Cited

U.S. PATENT DOCUMENTS

2011/0211665 A1* 9/2011 Maurer, Jr. .......... A61N 5/1039
378/19
2013/0142310 A1 6/2013 Fahimian et al.
2018/0085596 A1* 3/2018 Peltola ................ A61N 5/1081
2019/0134424 A1 5/2019 Dai et al.

FOREIGN PATENT DOCUMENTS

WO 2013/075743 A1 5/2013
WO 2015/039903 A1 3/2015
WO 2019/081042 A1 5/2019

OTHER PUBLICATIONS

"HyperArc a New Wave in Stereotactic Radiosurgery Solutions", https://www.varian.com/products/radiotherapy/treatment-planning/hyperarc, retrieved from internet on Oct. 9, 2020.

Jung et al., "A Method for Optimizing LINAC Treatment Geometry for Volumetric Modulated Arc Therapy of Multiple Brain Metastases", Aug. 2010.

"Multiple Brain Metastases 2.0", Software User Guide Revision 1.0, Brainlab, 2019.

"Hyperarc High-Definition Radiotherapy", https://www.varian.com/oncology/solutions/hyperarc, retrieved from internet on Jul. 29, 2019.

International Search Report and Written Opinion for corresponding International Application No. PCT/EP2020/070131, dated Oct. 6, 2020. 12 Pages.

* cited by examiner

COMPUTER-IMPLEMENTED MEDICAL METHOD FOR RADIATION TREATMENT (RT) PLANNING FOR TREATING MULTIPLE BRAIN METASTASES OF A PATIENT

RELATED APPLICATION DATA

This application is a national phase application of International Application No. PCT/EP2020/070131 filed Jul. 16, 2020, which claims priority to International Application No. PCT/EP2019/076214, filed on Sep. 27, 2019, the contents of both of which are incorporated herein by reference.

FIELD OF THE INVENTION

The present invention relates to a computer-implemented method for radiation treatment (RT) planning for treating multiple brain metastases of a patient, a corresponding computer program, a non-transitory program storage medium storing such a program and a computer for executing the program, as well as a medical system comprising an electronic data storage device and the aforementioned computer.

TECHNICAL BACKGROUND

For radiation treatment planning in the field of radiotherapy and/or radiosurgery, very sophisticated software programs are applied in order to find an appropriate or even the best radiation plan for the given medical and technical circumstances. In particular, such state of the art radiation treatment planning software solutions allow the medical practitioner to provide details about the following considerations to the software system.

Typically a planning target volume associated with or representing e.g. a metastasis is specified along with a desired prescribed dose. The prescribed dose should preferably be deposited in at least a partial volume, also referred to as coverage volume, of the planning target volume in order to ensure biological effectiveness of the irradiation treatment. Apart from that, one or more constraints to be fulfilled during irradiation treatment can be specified. Typically, an organ at risk like e.g. an eye of the patient, which preferably is to be spared during irradiation treatment or which should not receive more than an allowed dose in at least a partial volume thereof, can be specified as constraint. An optimization is carried out, which takes into account the specified planning target volume, a desired dose value defined by the radiologist, the one or more constraints, usually the coverage volume of the planning target volume is determined and a corresponding irradiation treatment plan is generated. This is done by an optimization algorithm, a so called optimizer, in the software that is available since years. The irradiation treatment plan can then be utilized to carry out the actual irradiation treatment.

However, particularly for multiple brain metastases treatment planning the difficulty arises how to define the arc setup, which is then used by the gantry of the radiation treatment apparatus to carry out the irradiation of the patient. Such an arc setup comprises a plurality of arcs, each arc being defined by a combination of a patient table angle, a gantry start angle and a gantry stop angle. In other words, an arc setup defines a set of arc trajectories, wherein each trajectory is defined by a gantry start and gantry stop angle and a unique table angle. Prior art solutions of Brainlab AG are described in e.g. the documents WO 2015/039903 A1 and WO 2013/075743 A1.

One available software solution of Brainlab AG called "Multiple Brain Mets SRS" software is a treatment planning software that produces treatment plans consisting of dynamic conformal arcs (a treatment modality for linac-based radiation therapy in which the linac head rotates around a patient, utilizing a gantry) with a single iso-center as described in WO 2013/075743 A1. Fields are collimated dynamically using a multi-leaf collimator while the gantry of the linac rotates around the patient's head. The fields are shaped according to projections of the metastases for a finite set of gantry angles (control points). For each control point, a projected shape can be either opened or blocked to alter the dose contribution. Moreover, a negative or positive 2D margin can be added to the projected shape to influence the dose profile. Finally, monitor units (arc-weights) must be set per arc (single rotation of the gantry). Monitor units are a measure of linac output and influence treatment time and efficiency.

The inventors identified the following for the treatment planning of multiple brain metastases using fixed arc setups. For dynamic conformal arc treatment plan optimization, several degrees of freedom are available, in particular 1) the arc setup, 2) the distribution of the target volumes, i.e. of the metastases, to the arcs, 3) arc-weights (monitor units), 4) opening or closing of a projected shape per control point and 5) a margin that can be set per metastasis per arc.

The existing software for multiple brain metastases "Multiple Brain Mets SRS", provides a solution to this problem by utilization of a dedicated optimization algorithm. The arc setup (degree of freedom 1) can be chosen by the user, but is not modified by the algorithm. Typically, the software assigns two arcs per table angle.

The first part of the algorithm is called "packing" and finds a suitable distribution of target volumes to arcs (degree of freedom 2) such that each metastasis is irradiated from as many different angles as possible. The second part of the algorithm referred to as "core optimization" uses degrees of freedom 3-5 to find a dose distribution which is optimal in terms of sufficient dose to the target volumes, preventing dose to normal tissue, and limiting dose to risk structures, i.e. organ at risks. An "optimizer" as used in prior art solutions can be used to carry out this "core optimization".

However, the existing software solution provides a solution for multiple brain metastases treatment planning, which is based on only manual definitions of the arc setups. Treatment planning in Brainlab AG's currently released Multiple Brain Mets SRS software is based on default arc setups. The optimization algorithm, as described above, always uses the predefined table and gantry definitions.

It is, therefore, desirable to provide for an improved radiation treatment planning for treating multiple brain metastases of a patient, e.g. allowing to automatically optimize arc setups for multiple brain metastases treatment planning of an individual patient.

The present invention can be used for radiotherapy or radiosurgery procedures, such as the cranial/spine stereotactic radiosurgery treatment planning system, e.g. in connection with a system for image-guided radiotherapy such as VERO® and ExacTrac®, all products of Brainlab AG.

Aspects of the present invention, embodiments, examples and exemplary steps are disclosed in the following. Different embodiments, examples and exemplary features of the invention can be combined in accordance with the invention wherever technically expedient and feasible.

EXEMPLARY SHORT DESCRIPTION OF THE INVENTION

The present invention defines a novel approach to automatically find an optimized arc setup. Such automatically optimized arc setup can then be used in the existing and aforementioned software solutions to carry out the "core optimization" thereby optimizing the degrees of freedom 3-5 to find the optimal dose distribution. The inventors of the present invention have found that using such an automatically optimized arc setup generally leads to an improved radiotherapy treatment plan. It should be noted that the present invention can of course be applied not only to multiple brain metastases, but to any other multiple targets within a human body.

According to the present invention, an initial, i.e. a first, packed arc setup is compared with one or more predefined arc setup constraints. These predefined arc setup constraints constrain at least one or more of the following parameters of the arc setup: the number of patient table angles per target volume, the number of passes, the sum of gantry span per metastasis over all arcs, the minimum table span, and the total number of patient table angles. Thus, one, two, three, four, or five, i.e. all, of said predefined arc setup constraints may be used for the comparison of the present invention. The user may select which of the constraints or which combination of said constraints he/she prefers in view of the present disclosure. Based on the result of the comparison between the first packed arc setup with the one or more of said predefined arc setup constraints a second arc setup is automatically suggested. The automatically suggested second arc setup may then be compared with the first one by calculating a score for both setups.

Preferably a minimum and maximum per used constraint may be defined. Thus, said predefined constraint about the number of patient table angles per target volume preferably defines a minimum and a maximum number of table angles per target volume if it is used, said predefined arc setup constraint about the number of times the gantry moves along one arc per patient table angle preferably defines a minimum and a maximum number of times the gantry moves along one arc per patient table angle if it is used. Moreover, the predefined arc setup constraint about the sum of gantry span per metastasis over all arcs preferably defines a minimum and a maximum sum of gantry span per metastasis over all arcs if it is used. Moreover, the predefined arc setup constraint about the total number of patient table angles preferably defines a minimum and a maximum number of the total number of patient table angles if it is used.

The present invention improves treatment efficiency and time by lowering the number of table angles and arcs for relatively easy geometries. It also improves treatment planning time by reducing the need for manual arc setup changes by the user and subsequent re-optimization of degrees of freedom 2-5. Moreover, the "core optimization" as described herein guarantees that the coverage is satisfied for each target volume. Therefore, it cannot be improved in principal. However, for an improved arc setup, as provided by the present invention, it is easier to sculp the prescription isodose around the shape of the target volume. We refer to this as target conformity. It also improves dose distribution in terms of limiting dose to risk structures by shortening arcs, closing projected shapes and adapting table angles to avoid irradiation through risk structures.

Several iterations of such a method can be carried out based on e.g. the comparison between an arc setup and the following, subsequent arc setup in the iteration. If this optimization is converging, which can be controlled by means of e.g. a predefined convergence criterion, this method of automatically finding an optimized arc setup may be stopped and the result may be further used in completely defining the radiotherapy treatment plan.

It should be notated that the presented method may be repeated in several iterations. Thus, the different embodiments explained herein after in detail may also be applied during such iterative repetitions of the presented method. In other words, the presented method can be repeated until a desired "quality" or grade of the finally suggested arc setup, i.e. the arc setup suggested by the presented method in the last iteration, is achieved.

In the following, a short description of the specific features of the present invention is given which shall not be understood to limit the invention only to the features or a combination of the features described in this section.

GENERAL DESCRIPTION OF THE INVENTION

In the following section, a description of the general features of the present invention is given, for example by referring to possible embodiments of the invention.

As stated above, it may be desirable to provide for an improved radiation treatment planning for treating multiple brain metastases of a patient, e.g. allowing to automatically optimizing arc setups for multiple brain metastases treatment planning of an individual patient.

This is achieved by the subject-matter of the independent claims, wherein further embodiments are incorporated in the dependent claims and the following description.

According to a first aspect of the present invention a computer-implemented medical method for radiation treatment (RT) planning for treating multiple brain metastases of a patient is presented. The method comprises the following steps:

acquiring a first arc setup comprising a plurality of arcs, each arc being defined by a combination of a patient table angle, a gantry start angle and a gantry stop angle (S1), distributing a plurality of target volumes, which describe the brain metastases, to the arcs of the first arc setup thereby providing a packed first arc setup (S2), comparing said first packed arc setup with one or more predefined arc setup constraints (S3), wherein the said one or more predefined arc setup constraints are selected from the following parameters: the number of patient table angles per target volume, the number passes, the sum of gantry span per metastasis over all arcs, the minimum table span, and the total number of patient table angles, and the method comprising the step of automatically suggesting at least a second arc setup based on a result of the comparison (S4).

This arc setup optimization algorithm is based on a definition of constraints, which shall be fulfilled for each suggested arc setup. In a preferred implementation, each new arc setup suggested by the presented method needs to decrease the number of violations of said constraints in order to be accepted. The reason is that the initial arc setup might violate already. The user may individually define these constraints based on the following findings of the inventors of the present invention.

Too less table angles would result in worse target volume coverage and/or higher normal tissue dose. Moreover, too many table angles would result in a long treatment time without substantial improvement in the dose distribution. Also, too less table angles would result in worse target volume coverage and/or higher normal tissue dose. Further, too many table angles would result in a long treatment time without substantial improvement in the dose distribution. Moreover, using multiple passes may improve the packing (distribution of target volumes to the arcs), which could be especially useful for clinics that want to limit the number of table angles for time duration reasons. In addition, a large gantry span (when distributed over multiple table angles) may improve target volume coverage and/or normal tissue dose, and a small gantry span per metastasis will result in more efficient deliveries. Considering a minimal table span makes sure that the optimization result remains stable and that target volumes are irradiated from a wide enough range of table positions.

Based on these findings and in view of the individual medical and technical setting the user is facing, the user may set the one or more constraints of the presented method accordingly. This allows a large flexibility of the presented method and it can be adapted to many different settings thereby using the guidance about the number of patient table angles per target volume, the number of passes, the sum of gantry span per metastasis over all arcs, the minimum table span, and the total number of patient table angles as detailed hereinbefore.

When using this guidance the user will be provided with an arc setup suggested by the present invention that improves treatment efficiency and time by lowering the number of table angles and arcs for relatively easy geometries. The arc setup suggested by the present invention also improves treatment planning time by reducing the need for manual arc setup changes by the user and subsequent re-optimization of degrees of freedom 2-5. Moreover, the "core optimization" as described herein guarantees that the coverage is satisfied for each target volume. Therefore it cannot be improved in principal. However, for an improved arc setup, as provided by the present invention, it is easier to sculpt the prescription isodose around the shape of the target volume. We refer to this as target conformity. It also improves dose distribution in terms of limiting dose to risk structures by shortening arcs, and adapting table angles to avoid irradiation through risk structures.

The predefined arc setup constraints may be either pre-set by the manufacturer based on retrospective treatment plan analysis or can be made user definable.

Moreover, the method may heuristically and stochastically propose one or multiple new arc setups, as will be explained hereinafter in the context of detailed embodiments.

It should be noted that the present invention can of course be applied not only to multiple brain metastases, but to any other targets to be irradiated within a human body.

The new arc setup or setups, which are suggested by the presented method, may then be evaluated and compared to first or previous setups and may also be compared as to their score after a packing has been carried out for them and after the packed versions of these new arc setups are scored, i.e. a score is calculated. This aspect of repacking the new arc setups and for calculating a score for the repacked new arc setups to compare them and/or to evaluate whether the score converges during several iterations of the presented method, can be gathered from e.g. the embodiment of FIG. 6.

In the context of the present invention the term "pass" shall be understood in that each pass is uniquely described by a table angle (plus gantry start and stop angle) and the set of target volumes it has "packed" (i.e. irradiates). In an embodiment one can keep gantry start and stop the same for each table angle. If there exist multiple passes per table angle, this means that these must have a different set of target volumes. And it should be noted that these sets might overlap. Depending on machine constraints, it might actually take multiple arcs to irradiate all monitor units for a pass. Different passes may distinguish from each other in which metastases is irradiated, which time is used to move the gantry along the arc and also which gantry start and/or stop angles are used.

Moreover, in the context of the present invention the term "sum of gantry span per metastasis over all arcs" shall be understood as the sum of all gantry angles for one particular metastasis when summarized over all arcs of an arc setup.

Further, in the context of the present invention the term "packing" shall be understood as the process of determining which metastasis will be irradiated on which arc or arcs of one particular arc setup, which is well in line with the common understanding of the skilled person. In this sense, it is disclosed herein that distributing a plurality of target volumes, which describe the brain metastases, to the arcs of a first arc setup provides a packed first arc setup. Existing solutions/algorithms for carrying out such "packing" are well known to the skilled reader and he/she may of course make use of this knowledge when using the present invention. The user may, for example use, the available software solution of Brainlab AG called "Multiple Brain Mets SRS" software, in which such a packing is comprised. However, also other solutions may be used. For example in FIGS. 3 and 4 it can be gathered how a plurality of target volumes, i.e. metastases, are distributed over the arcs.

As is clear to the skilled reader the data describing or defining the metastases of a patient may be provided in digital form like e.g. in the form of Image data like e.g. MRI data. In such medical imaging data a contouring could be carried out thus specifically defining the metastasis for the practitioner and or for the computer applying the method presented herein.

The term "arc-weight" or "monitor units" shall be understood as a value that is proportional to the photons which the radiation source of the radiation treatment apparatus emits for one particular arc. Thus, this value is a measure of the energy, which is applied to or placed into the patient during this particular arc.

Further, in the context of the present invention the term "control point" is defined by a combination of the following radiotherapy parameters: the gantry angle, the patient table angle, the positions of the leaves of the leaf collimator used to shape the radiation field, the rotational position of the leaf collimator and the monitor units.

Further, in the context of the present invention the term "total field size" shall be understood as the sum of the surface of all leaf openings over all control points.

It should also be noted that the application of leaf collimators in the field of radiotherapy are well known by the skilled person and it is exemplarily referred here to Brainlab AG's patent application WO 2013/075743 where its described in the context of FIGS. 3 and 4 how the leaves can be adjusted to target the target volume, i.e. one or more metastases.

The expression "acquiring a first arc setup" for example encompasses the scenario in which the arc setup is selected by user on a user interface. It may be the case that the user selects a "default" arc setup out of a plurality of setups that are pre-stored in a RT planning software like "Multiple Brain Mets SRS" mentioned hereinbefore. However, also other scenarios may be understood as acquiring a first or second or third etc. arc setup. For example, an automatically defined initial arc setup may be selected by the computer. In a second iteration of the presented method, the step of acquiring the arc setup can be embodied by using the suggested second arc set up, which is provided in the first iteration by the method.

According to another exemplary embodiment for each of the one or more predefined arc setup constraints, which is actually used in the individual case, a minimum and a maximum, e.g. a minimum and a maximum value, is defined and used during the comparison of the first packed arc setup with the (one or more) predefined arc setup constraints. If one constraint is used a minimum and maximum for said constraint parameter is used, if two constraints are used, a minimum and maximum for both constraint parameters is used, respectively etc. This will be explained in more detail hereinafter the context of a detailed embodiment.

According to another exemplary embodiment, the pre-defined arc setup constraint about the number of patient table angles defines a minimum number of patient table angles. And if the result of the comparison of the first packed arc setup with the one or more predefined arc setup constraints is that the minimum of the number of patient table angles is not violated, the method comprises the step of removing a patient table angle from the first arc setup. If this yields an arc setup with a decreased number of violated constraints, this new arc setup may be then used for further optimization e.g. using the present invention, or if it is decided that this shall be the final arc setup it may be used as RT plan for irradiating the metastases of the patient with an RT apparatus. Note that such a final arc setup can then be subject to core optimization, as exemplarily shown in FIG. 6 with 605, before an RT is generated. However, during core optimization 605 the arc setup will not change anymore. Alternatively, or in addition thereto, in the method the predefined arc setup constraint about the number of passes defines a minimum number of passes, and if a result of the comparison of the first packed arc setup with the one or more predefined arc setup constraints is that the minimum of the number of passes is not violated, the method comprises the step of removing a pass from the first arc setup. If this yields an arc setup with a decreased number of violated constraints, this new arc setup may be then used for further optimization e.g. using the present invention, or if it is decided that this shall be the final arc setup it may be used as RT plan for irradiating the metastases of the patient with an RT apparatus. It should again be noted that said final arc setup can then be subject to core optimization, as exemplarily shown in FIG. 6 with 605, before an RT is generated. However, during core optimization 605 the arc setup will not change anymore. This holds true in general and such a core optimization can be applied in any embodiment mentioned herein, especially in the embodiments where such a final arc setup is mentioned hereinafter.

For example, in the embodiment shown in FIG. 6 in 602, if for a target volume a minimum constraint is not violated a removal of pass/table is generated in 603. However, the decision whether this actually results in an overall decreased number of violated constraints is done after performing step 604, as this performs a new packing and might change the whole distribution of target volumes to arcs.

It must be noted that the feature "the predefined arc setup constraint about the number of patient table angles defines a minimum number of patient table angles" covers the parameter of "the number of patient table angles per target volume", and also covers additionally or alternatively (i.e. and/or) the parameter of the "total number of patient table angles".

In other words, it is automatically calculated, whether a removal of a patient table angle and/or a pass from the first arc setup leads to an arc setup, with which less of the predefined arc setup constraints will be violated. If this is affirmed, then the patient table angle and/or the pass is removed from the first arc setup or the previous arc setup in case it is a further iteration of the presented method.

Thus, in this embodiment it is determined whether the pre-defined minimum of the number of patient table angles is violated by comparing the first packed arc setup with this minimum number. And if this is not the case, i.e. if it is found that no such violation is present, then it is determined whether the removal of a patient table angle from the first packed arc setup will lead to a new packed arc setup, with which at least one violation of the one or more pre-defined arc setup constraints, that was present for the first/previous packed arc setup, can be avoided. In this sense, such a removal of a patient table angle from the first/previous packed arc setup would lead to a new arc setup with a decreased number of violated constraints. The same principle applies and holds true of course for the removal of a pass.

In case both a patient table angle and a pass is removed this may be done so as to create only a single one new arc setup, i.e. the suggested second arc set up. But in another embodiment, also two new arc setups may be suggested, wherein the first new suggested arc setup differs from previous (e.g. the initial, i.e. first) arc set up in one removed patient table angle, whereas the second new suggested arc setup differs from the previous (e.g. initial, i.e. first) arc set up in one removed pass. The latter embodiment can be easily gathered from the detailed embodiment described in the context of FIG. 6, which will be described in more detail herein below. It should be noted that also more than two new arc setups may be generated during this suggestion, namely by removing for another new arc setup more than one table or another table as compared to the first removal. The same holds true for the removal of passes. Thus, speaking generally, a plurality of new arc setups may be created by the removal of one or more tables and/or one or more passes. This will become apparent from a further embodiment that will be described in detail herein below. This will be explained in more detail hereinafter the context of a detailed embodiment.

According to another exemplary embodiment the removal of the patient table angle and/or of the pass from the first arc setup is based on the number of target volumes packed to an arc. Furthermore, the removal of the patient table angle and/or of the pass is carried out in a manner such that patient table angles or passes with the lowest number of packed target volumes and/or with lowest total field size are removed first.

In this embodiment, a heuristic removal of the patient table angle and/or of the pass is specified. Further, as described herein before, the term "total field size" shall be understood as the sum of the surface of all leaf openings over all control points. Thus, by taking into account the patient table angles and/or passes with the lowest total field size, an efficient radiotherapy treatment plan with minimal number of arcs can be achieved. This holds true since a large total field size means that many metastases are irradiated at the same time and hence a faster irradiation can be achieved. Thus, a second arc setup that is suggested by this embodiment, which will lead to an improved arc setup and finally to an improved radiotherapy treatment plan. This will be explained in more detail hereinafter the context of a detailed embodiment.

According to another exemplary embodiment the method further comprises the step of randomly selecting at least one pass of the first arc setup for being removed from the first arc setup.

In this embodiment, the pass, which shall be removed from the first arc setup is selected in a random manner. The computer may do this automatically and the skilled person knows how to implement such a random selection. The aspect of the random configuration proposition is also depicted in the detailed embodiment shown in and described in the context of FIG. 6.

According to another exemplary embodiment the method further comprises the step of reordering after the removal of said patient table angle, the remaining patient table angles of the second arc setup, preferably in an equidistant manner.

In other words, the patient table angles, which remain after the removal in the arc setup suggested by the present invention, will be reordered. Different criteria may be applied how the reordering shall be carried out and the user may select his preferred criterion. However, in a preferred embodiment the reordering is carried out in an equidistant manner. If for example, the currently evaluated arc setup, e.g. the first arc setup, comprises the following 6 patient table angles, 10°, 12°, 35°, 42°, 50° and 60°, and the step of removing at least one patient table angle removes the 12° angle, then the remaining 5 patient table angles are reorder for the second, suggested arc set up to the following patient table angles: 10°, 20°, 30°, 40°, 50° and 60°. In other words, the angles to be used during RT irradiation are equally spread over the current span of 40°.

According to another exemplary embodiment, in the predefined arc setup constraint about the patient table angle a maximum number of patient table angles is defined. And if a result of the comparison of the first packed arc setup with the one or more predefined arc setup constraints is that the maximum number of patient table angles is not violated, the method comprises the step of adding a patient table angle to the first arc setup. If this yields an arc setup with a decreased number of violated constraints, this new arc setup may be then used for further optimization e.g. using the present invention, or if it is decided that this shall be the final arc setup it may be used as RT plan for irradiating the metastases of the patient with an RT apparatus. Alternatively, or in addition thereto the predefined arc setup constraint about the number of passes defines a maximum number of passes. And if a result of the comparison of the first packed arc setup with the one or more predefined arc setup constraints is that the maximum number of passes is not violated, the method comprises the step adding a pass to the first arc setup. If this yields an arc setup with a decreased number of violated constraints, this new arc setup may be then used for further optimization e.g. using the present invention, or if it is decided that this shall be the final arc setup it may be used as RT plan for irradiating the metastases of the patient with an RT apparatus.

It must be noted that the feature "the predefined arc setup constraint about the number of patient table angles defines a maximum number of patient table angles" covers the parameter of "the number of patient table angles per target volume", and also covers additionally or alternatively (i.e. and/or) the parameter of the "total number of patient table angles".

In this embodiment, it is determined whether the predefined maximum of the number of patient table angles is violated by comparing the first packed arc setup with this maximum number. And if this is not the case, i.e. if it is found that no such violation is present, then it is determined whether the addition of a patient table angle to the first packed arc setup will lead to a new packed arc setup, with which at least one violation of the one or more pre-defined arc setup constraints, that was present for the first/previous packed arc setup, can be avoided. In this sense, such an addition of a patient table angle to the first/previous packed arc setup would lead to a new arc setup with a decreased number of violated constraints. The same principle as was just explained for the addition of a patient table angle applies and holds true of course also for the addition of a pass.

In case both a patient table angle and a pass is added this may be done so as to create only one new arc setup, i.e. the suggested second arc set up. But in another embodiment, also two new arc setups may be suggested, wherein the first new suggested arc setup differs from the previous (e.g. initial, i.e. first) arc setup in one added patient table angle, whereas the second new suggested arc setup differs from the previous (e.g. initial, i.e. first) arc setup in one added pass. The latter embodiment can be easily gathered from the detailed embodiment described in the context of FIG. 6, which will be described in more detail herein below. It should be noted that also more than two new arc setups may be generated during this suggestion, namely by adding for another new arc setup more than one table or another table as compared to the first addition. The same holds true for the addition of passes. Thus, speaking generally, a plurality of new arc setups may be created by the addition of one or more tables and/or one or more passes. This will become apparent from a further embodiment that will be described in detail herein below.

According to another exemplary embodiment, the predefined arc setup constraint about the number of patient table angles per target volume defines a minimum and a maximum number of table angles per target volume, the predefined arc setup constraint about the number of times the gantry moves along one arc per patient table angle defines a minimum and a maximum number of times the gantry moves along one arc per patient table angle, the predefined arc setup constraint about the sum of gantry span per metastasis over all arcs defines a minimum and a maximum sum of gantry span per metastasis over all arcs, and the total number of patient table angles defines a minimum and a maximum number of the total number of patient table angles.

The user of the present invention may use the following exemplary embodiment as a default setting, but he may also amend the following examples of predefined arc setup constraints.

The number of table angles (i.e. patient table angles) per target volume, can be set, e.g. in a corresponding software to values like for example minimum 3 and maximum 4. As explained before the inventors of the present invention found that too less table angles would result in worse target volume coverage and/or higher normal tissue dose. Moreover, too many table angles would result in a long treatment time without substantial improvement in the dose distribution. Further, too many table angles would result in a long treatment time without substantial improvement in the dose distribution. In addition, the number of passes per table angle could be set in the corresponding software to e.g. minimum 1 and maximum 4, because using multiple passes may improve the packing (distribution of target volumes to the arcs), which could be especially useful for clinics that want to limit the number of table angles for time duration reasons. Moreover, the sum of gantry span per metastasis over all arcs can be set to e.g. minimum 450 degrees and maximum 650 degrees, a large gantry span may improve target volume coverage and/or normal tissue dose, a small gantry span per metastasis will result in more efficient deliveries. It is clear to the skilled reader that also other values for the minimum and maximum constraints can be chosen when using the presented embodiment.

It should be noted by the user that the total number of table angles can be set to, for example, minimum 3 and maximum 10, since too less table angles would result in worse target volume coverage and/or higher normal tissue dose. It goes without saying that the user may set the minimum and the maximum to different values as presented here. Using the guidance that too less table angles would result in worse target volume coverage and/or higher normal tissue dose, the medical practitioner can select these values based on the individual medical setting of a particular patient. The subsequent automatic suggestion carried out by the computer-implemented medical method of the present invention will then lead to an improved arc setup.

In a preferred embodiment the minimal table span may be set to e.g. 90 degrees, ensuring that the optimization result remains stable and that target volumes are irradiated from a wide enough range of table positions. This further improves the arc setup suggested by the present invention, which can subsequently be used for defining the radiotherapy treatment plan for a particular patient.

According to another exemplary embodiment it is automatically checked if a result of the comparison of the first packed arc setup with the predefined arc setup constraints is that none of the constraints of
   a. the minimum number of patient table angles per target volume,
   b. the minimum number of times the gantry moves along one arc per patient table angle,
   c. the minimum sum of gantry span per metastasis over all arcs
   d. the minimum number and a maximum number of the total number of patient table angles,
are violated. If no violation is detected by the computer and/or software the method proceeds with the step of removing a patient table angle and/or a pass from the first arc setup. If this yields an arc setup with a decreased number of violated constraints, this new arc setup may be then used for further optimization e.g. using the present invention, or if it is decided that this shall be the final arc setup it may be used as RT plan for irradiating the metastases of the patient with an RT apparatus.

In other words, it is automatically calculated, if said conditions are fulfilled, whether a removal of a patient table angle and/or a pass from the first arc setup leads to an arc setup, with which less of the predefined arc setup constraints will be violated. If this is affirmed, then the patient table angle and/or the pass is removed from the first arc setup or the previous arc setup in case it is a further iteration of the presented method.

As was disclosed hereinbefore, a patient table angle and/or a pass is only removed from the first arc setup in this embodiment, if the comparison results in that none of the "minimum number" of each mentioned constraint is violated and if the new arc setup, i.e. with the one table angle and/or a pass being removed, leads to a decreased number of violated constraints. Hence, it may be the case, just as an illustrative example, that the first arc set up does not violate any of the "minimum number" of each constraint, but violates the maximum number of e.g. the constraint a) "patient table angles per target volume" and in this example also violates the maximum number of the constraint b) "number of times the gantry moves along one arc per patient table angle". In such a scenario, this embodiment teaches to remove at least one (or more) patient table angles and/or passes from the first arc set up and the software checks whether this leads to an arc set up with only one or even none violated maximum constraints. Thus, in this example, one or two violations of constraints can beneficially be avoided with said new arc setup compared to the first arc setup.

As is clear to the skilled reader, the new arc setup that can be generated with this algorithm will preferably have a decreased number violations with respect to the maximum number of patient table angles per target volume, and/or the maximum number of times the gantry moves along one arc per patient table angle, and/or the maximum sum of gantry span per metastasis over all arcs. This will be explained in more detail hereinafter in the context of specific embodiments.

In case both a patient table angle and a pass is removed this may be done so as to create only a single one new arc setup, i.e. the suggested second arc set up. But in another embodiment, also two new arc setups may be suggested, wherein the first new suggested arc setup differs from previous (e.g. the initial, i.e. first) arc set up in one removed patient table angle, whereas the second new suggested arc setup differs from the previous (e.g. initial, i.e. first) arc set up in one removed pass. The latter embodiment can be easily gathered from the detailed embodiment described in the context of FIG. 6, which will be described in more detail herein below. It should be noted that also more than two new arc setups may be generated during this suggestion, namely by removing for another new arc setup more than one table or another table as compared to the first removal. The same holds true for the removal of passes. Thus, speaking generally, a plurality of new arc setups may be created by the removal of one or more tables and/or one or more passes. This further improves the arc setup suggested by the present invention, which can subsequently be used for the core optimization and finally for defining the radiotherapy treatment plan for a particular patient. This will become apparent from a further embodiment that will be described in detail herein below.

According to another exemplary embodiment, the method further comprises the step of randomly selecting at least one pass of the first arc setup for being removed from the first arc setup by step S9, which will be described in the context of FIG. 2 later on in more detail.

In this embodiment, the pass, which shall be removed from the first arc setup is selected in a random manner. The computer may do this automatically and the skilled person knows how to implement such a random selection. The aspect of the random configuration proposition is also depicted in the detailed embodiment shown in and described in the context of FIG. 6.

In a preferred embodiment the pass with the lowest number of packed target volumes is removed and in addition also one pass, which is randomly selected, is removed.

In a further embodiment patient table angles and/or passes are randomly selected for removal out of the group comprising patient table angles and/or passes with the lowest number of packed target volumes and/or with lowest total field size, patient table angles and/or passes with the second lowest number of packed target volumes and/or with the second lowest total field size, and patient table angles and/or passes with the third lowest number of packed target volumes and/or with the third lowest total field size.

According to another exemplary embodiment, the method further comprises reordering, after the removal of said patient table angle, the remaining patient table angles of the second arc setup, preferably in an equidistant manner.

According to another exemplary embodiment, it is checked if a result of the comparison of the first packed arc setup with the one or more predefined arc setup constraints is that none of the constraints of the maximum number of table angles per target volume, the maximum number of times the gantry moves along one arc per table angle, the maximum sum of gantry span, the maximum number of the total number of patient table angles, and the maximum of the total patient table angle is violated. If not violation is present the method comprises the step of adding a patient table angle and/or a pass to the first arc setup. If this yields an arc setup with a decreased number of violated constraints, this new arc setup may be then used for further optimization e.g. using the present invention, or if it is decided that this shall be the final arc setup it may be used as RT plan for irradiating the metastases of the patient with an RT apparatus.

As was disclosed hereinbefore, a patient table angle and/or a pass is only added from the first arc setup, if the comparison results in that none of the "maximum number" of each mentioned constraint is violated and if the new set up, i.e. with the one table angle and/or a pass being added, leads to a decreased number of violated constraints. Hence, it may, just as an illustrative example, be the case that the first arc set up does not violate any of the "maximum number" of each constraint, but violates the minimum number of the constraint a) "patient table angles per target volume" and also violates the minimum number of the constraint b) "number of times the gantry moves along one arc per patient table angle". In such a scenario, this embodiment teaches to add at least one or more patient table angles and/or passes from the first arc set up and the software checks whether this leads to a new arc set up with only one or even none violated minimum constraints. Thus, in this example, one or two violations of constraints can beneficially be avoided with said new arc setup compared to the first arc setup.

As is clear to the skilled reader, the new arc setup that can be generated with this algorithm will preferably have a decreased number violations with respect to the minimum number of table angles per target volume, the minimum number of times the gantry moves along one arc per table angle, the minimum sum of gantry span, the minimum number of the total number of patient table angles, and/or the minimum of the total patient table angle. This will be explained in more detail hereinafter in the context of specific embodiments.

In case both a patient table angle and a pass is added this may be done so as to create only one new arc setup, i.e. the suggested second arc set up. But in another embodiment, also two new arc setups may be suggested, wherein the first new suggested arc setup differs from the previous (e.g. initial, i.e. first) arc setup in one added patient table angle, whereas the second new suggested arc setup differs from the previous (e.g. initial, i.e. first) arc setup in one added pass. The latter embodiment can be easily gathered from the detailed embodiment described in the context of FIG. 6, which will be described in more detail herein below. It should be noted that also more than two new arc setups may be generated during this suggestion, namely by adding for another new arc setup more than one table or another table as compared to the first addition. The same holds true for the addition of passes. Thus, speaking generally, a plurality of new arc setups may be created by the addition of one or more tables and/or one or more passes. This further improves the arc setup suggested by the present invention, which can subsequently be used for e.g. the core optimization and finally for defining the radiotherapy treatment plan for a particular patient. This will become apparent from a further embodiment that will be described in detail herein below.

According to another exemplary embodiment, in the method step S4, i.e. automatically suggesting at least a second arc setup based on a result of the comparison, a plurality of arc setups are suggested based on the result of the comparison, wherein for a first one of the plurality of suggested arc setups a patient table angle is removed from the first arc setup, a second one of the plurality of suggested arc setups a pass is removed from the first arc setup, a third one of the plurality of suggested arc setups a patient table angle is added to the first arc setup, a fourth one of the plurality of suggested arc setups a pass is added to the first arc setup, and wherein for a fifth one of the plurality of suggested arc setups a random change of at least one patient table angle of the first arc setup.

The way to decide which table angle and/or pass is to be added or is to be removed may follow the criteria set out herein, but also other criteria may be used. Moreover, these criteria, either the ones mentioned herein or also other ones, may be supplemented with the concept of randomly adding or removing table angles and/or passes.

The new arc setups, which are suggested by the presented method, may then be evaluated and compared to first the predefined arc set-up constraints and may also be compared as to their score after a packing has been carried out for them and after the packed versions of these new arc setups are scored. This aspect of repacking the new arc setups and of calculating a score for the repacked new arc setups to compare them and/or to evaluate whether the score converges during several iterations of the present method, will be explained in more detail hereinafter, e.g. in the context of the embodiment of FIG. 6.

According to another exemplary embodiment, the addition of the patient table angle and/or of the pass from the first arc setup is based on the number of target volumes packed to an arc, and wherein the addition of the patient table angle and/or of the pass is carried out in a manner such that the number of target volumes packed to an arc and/or total field size are locally increased.

Increasing the number of target volumes packed to an arc increases the efficiency of the corresponding RT treatment plan, since many target volumes, like e.g. metastases, can be irradiated during only one arc. Moreover, in the context of the present invention the term "locally increasing the total field size" shall be understood as increasing the total field size for a patient table angle or for an angular region around said patient table angle. Said angular region may be defined by the user. As is understood by the skilled reader, the guidance behind this embodiment is that when all arcs in one angular region, e.g. in the region from 10° to 60° patient table angle, already enough/all metastases are irradiated, no further arc in this angular region is needed.

According to another exemplary embodiment, the method further comprises the step of reordering the patient table angles of the arc setup with the added patient table angle, preferably in an equidistant manner.

In other words, the patient table angles with the new patient angle will be reordered. Different criteria may be applied how the reordering shall be carried out and the user may select his preferred criterion. However, in a preferred embodiment the reordering is carried out in an equidistant manner, as has been explained hereinbefore in detail for the embodiment of removing table angles. It is thus kindly referred to this embodiment here for the description of the reordering in an equidistant manner.

According to another exemplary embodiment, the method further comprises calculating a first score for the first packed arc setup (S5), distributing the plurality of target volumes, which describe the brain metastases, to the arcs of the suggested second arc setup thereby providing a packed second arc setup (S6), calculating a second score for the packed second arc setup (S7), and comparing the first and second scores (S8).

This embodiment introduces the calculation of a score, e.g. an objective score, of a packed arc setup. Thus, this embodiment describes the calculation of a first score, e.g. a first value, for the first packed arc setup and a second score, i.e. a second value, for the suggested arc setup, which is packed after it was suggested. The two scores can then be compared to decide upon the further procedure, for example, whether to already use the suggested second arc set up or to further optimize the second arc setup with the method of the present invention presented herein. This aspect can also be gathered from the detailed embodiment example of FIG. 6.

In order to calculate a score of a packed arc setup, a mathematical function may be used that takes several parameters into account. It should be noted that the use of such scores can be understood as calculating a "packing objective score". Said "packing objective score" may be defined as follows in an exemplary embodiment. The advantage of one packed arc setup over another, expressed by such a score, can be defined by evaluating the following parameters:

1. The number of tables angles per target volume (e.g., irradiating from three table angles typically results in better conformity than one table angle) and
2. The dosimetric impact of the control points on the target volume (i.e., irradiating target volumes from an angle closer to the radiation source shall be preferred over angles for which the source is further away).

The objective function used to calculate said score may consist in an exemplary embodiment of e.g. the following terms:

1. The number of table angles for each target volume (shall be maximized).
2. Average number of table angles over all target volumes (shall be maximized).
3. Dosimetric impact for each target volume (shall be maximized).
4. Average dosimetric impact over all target volumes (shall be maximized).
5. Number of control points per target volume that are outside the jaw field (shall be minimized).
6. Average number of control points that are outside the jaw field over all target volumes (shall be minimized).
7. Number of control points per target volume that use thick leaves (shall be minimized).
8. Average number of control points that use thick leaves over all target volumes (shall be minimized.

It should be noted that terms 7 and 8 are only relevant for MLCs with different leaf widths. Depending on how these parameters are weighed, the mathematical relationship used will be defined. Thus, by using a mathematical function for calculating a score of an arc setup allows an easy comparison between different arc setups.

According to another exemplary embodiment, the method further comprises the step of repeating steps S1 to S8, as mentioned hereinbefore and in the claims, in several iterations until the calculated score of a final arc setup, which was automatically suggested during a final iteration of said several iterations, fulfils a predefined convergence criterion.

This embodiment teaches to repeat at least the steps of the presented method, at least the ones defined in claim 1, in several iterations. Also the other additional steps mentioned herein and defining further embodiments may be repeated during several iterations. In other words, the presented method can be repeated until a desired "quality" or grade of the finally suggested arc setup, i.e. the arc setup suggested by the presented method in the last iteration, is achieved. Thus, the method starts with the "first arc setup" then suggests according to the method described herein at least a second arc set up. This suggested second arc setup may then be used in the next iteration, i.e. the second iteration, for the packing step in method step S2 and the following comparison in step S3. After this comparison with the predefined arc setup constraints a third arc setup may be suggested by the method. In the same manner, the suggested third arc setup may then be used for the packing step in method step S2 and the following comparison in step S3 of the next, i.e. the third iteration. As is clear to the skilled reader plurality of iterations may be carried out in this manner.

It should be noted that in an embodiment, the predefined arc setup constraints are kept unchanged and are thus identical for all the iterations.

Moreover, it should be noted that many possibilities exist to implement the predefined convergence criterion according to which the iterative method is finished. For example, a target score or minimum score may be predefined and each arc setup, which is suggested during an iteration of the presented method, is packed and then a score is calculated for the packed suggested arc setup. This score can then be compared to e.g. said predefined target score or minimum score. In case the score of said arc setup is at least equal to said predefined target score or minimum score the method may consider that the "predefined convergence criterion" is fulfilled. Thus, speaking generally, the new arc setup or setups, which are suggested by the presented method, may be evaluated and compared with their calculated score after a packing has been carried out for them. This aspect of repacking the new arc setups and for calculating a score for the repacked new arc setups to compare them and/or to evaluate whether the score converges during several iterations of the present method, can also be gathered from e.g. the embodiment of FIG. 6. Of course, other conditions may be set by the user to finish the iterative method described herein.

According to another exemplary embodiment, the method further comprises the step for the final arc setup:

optimizing at least one, and preferably all, of the following parameters
 a. the arc-weight, i.e. monitor units, for each arc of the final arc setup,
 b. the positions of leaves of a leave collimator of an RT apparatus, and
 c. the margin, either a positive or negative margin, per target volume and per arc.

Identifying an improved arc setup using the present invention, as is described at least in claim 1 by steps S1 to S4, may be seen as a first part of the computer-implemented medical method described by this embodiment. The optimization of at least one or all of the parameters arc weight, leaves position and margins may then be seen as the second part of the method or algorithm. This second part of the method (referred to as "core optimization") uses the degrees of freedom a.-c. to find a dose distribution which is optimal in terms of sufficient dose to the target volumes, preventing dose to normal tissue and limiting dose to risk structures. It should be noted that a negative or positive 2D margin can be added to the projected shape to influence the dose profile.

It should be noted that this core optimization may already be carried out for the suggested second arc setup provided already after the first iteration of the presented method.

According to another exemplary embodiment, the method further comprises the step of using the final arc setup or a result of the optimization as RT plan for irradiating the metastases of the patient with/for the RT apparatus.

In this embodiment it is added that the result of the present invention is used in an RT plan.

According to another exemplary embodiment, the automatic suggestion is a heuristical suggestion of at least one new arc setup and preferably comprises a stochastical suggestion of at least one new arc setup.

A detailed version thereof has been described hereinbefore for the removal of passes, where in a preferred embodiment the pass with the lowest number of packed target volumes is removed and in addition also one pass, which is randomly selected, is removed.

According to another exemplary embodiment, a random change of a patient table angle of the first arc setup is generated for the suggested second arc setup regardless of a result of the comparison between the first packed arc setup and the one or more predefined arc setup constraints.

It is defined in these embodiments that the suggestion of the second arc setup in step S4, as explained in e.g. claim 1, is a heuristic and a stochastic suggestion with a random change of a patient table angle. The inventors of the present invention found that where finding an optimal solution is impossible or impractical, this heuristic method can be used to speed up the process of finding a satisfactory solution of an improved arc setup that leads to an at least improved RT treatment plan as compared to the prior art, as it was described in the beginning.

According to another exemplary embodiment, the generated change of patient table angle takes into account one or more predefined risk structures, i.e. one or more organ at risk of the patient.

Typically, an organ at risk, which preferably is to be spared during irradiation treatment or which should not receive more than an allowed dose in at least a partial volume thereof, can be specified as constraint by the user.

In the following, another embodiment of the presented method and its context will be explained in detail. The inventors of the present invention have also found that there is a relation between the number of table angles per target volume and the achieved target conformity/normal tissue dose. In general, increasing the number of table angles per target volumes improves conformity and reduces normal tissue dose. However, the effect of improved dosimetry quickly converges and conflicts with the goal of reducing the treatment time. In the context of this invention, it can be of interest to automatically find the minimal number of table angles which results in sufficient conformity and acceptable normal tissue dose such that increasing the number of table angles would not result in a substantial dosimetric improvement. It was established by the inventors that the before mentioned effect can differ between target volumes. Therefore, using the same minimum and maximum value of the constraint for each target volume cannot in general result in an optimal trade-off between treatment delivery efficiency and dosimetric results. This embodiment introduces an automatic solution, i.e. an embodiment of the method of the present invention, to find constraint values for each individual target volume. Ideally, the automatic solution removes the necessity that the user of the software has to explore the constraint values manually.

Thus, in this embodiment the method comprises the step of automatically determining the table angle per target volume constraints.

The inventors of the present invention found that there is a correlation between the geometry of patient anatomy/disease and the preferred number of table angles per target volume. The geometric description of the patient may include proximity between target volumes, proximity to risk organs, sphericity, convexity, diameter, volume and other geometric features. The inventors identified two beneficial approaches to finding a function which maps geometric parameters to values for the table angle per target volume constraint.

Thus, in a first preferred embodiment, a mapping function is established by simulating treatment plans with different arc setup for a patient dataset. The resulting treatment plans shall cover various differing number of constraints. This allows the deduction of appropriate constraint values and can be performed as part of product development, notably without user interaction. The definition of the function can be performed using various method, e.g. data learning or rule-based.

And in a second preferred embodiment, a mapping function is established by a retrospective study of clinical treatment plans. This allows inspecting the trade-off between table angles and dosimetric results as deemed clinically acceptable by clinical staff and can be performed either during product development or as part of the product. The definition of the function can be performed using various method, e.g. data learning or rule-based.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect. The invention may alternatively or additionally relate to a (physical, for example electrical, for example technically generated) signal wave, for example a digital signal wave, carrying information which represents the program, for example the aforementioned program, which for example comprises code means which are adapted to perform any or all of the steps of the method according to the first aspect. A computer program stored on a disc is a data file, and when the file is read out and transmitted it becomes a data stream for example in the form of a (physical, for example electrical, for example technically generated) signal. The signal can be implemented as the signal wave which is described herein. For example, the signal, for example the signal wave is constituted to be transmitted via a computer network, for example LAN, WLAN, WAN, for example the internet. The invention according to the second aspect therefore, may alternatively or additionally relate to a data stream representative of the aforementioned program.

In a third aspect, the invention is directed to a non-transitory computer-readable program storage medium on which the program according to the second aspect is stored.

In a fourth aspect, the invention is directed to a medical system, comprising:

d) the at least one computer according to the second aspect;

e) at least one electronic data storage device storing at least patient data describing the multiple brain metastases of the patient; and
f) a medical device for carrying out a medical procedure on the patient,
wherein the at least one computer is operably coupled to
the at least one electronic data storage device for acquiring, from the at least one data storage device, the patient data describing the multiple brain metastases of the patient, and
the medical device for issuing a control signal to the medical device for controlling the operation of the medical device on the basis of an arc setup suggested according to the method presented herein.

According to an exemplary embodiment, the medical device comprises a radiation treatment (RT) apparatus comprising a treatment beam source and a patient support unit, wherein the at least one computer is operably coupled to the radiation treatment apparatus for issuing a control signal to the radiation treatment apparatus for controlling, on the basis of an arc setup suggested according to any of the previously described methods, at least one of the operation of the treatment beam source or the position of the patient support unit.

An exemplary system is a radiotherapy or radiosurgery system, e.g. ExacTrac.

In an example of the system according to the fourth aspect, the medical device comprises a radiation treatment apparatus comprising a treatment beam source and a patient support unit (such as at least one of a patient table or a headrest). The at least one computer is then operably coupled to the radiation treatment apparatus for issuing a control signal to the radiation treatment apparatus for controlling, on the basis of the suggested second arc setup.

For example, the invention does not involve or in particular comprise or encompass an invasive step, which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. The invention is instead directed as applicable to optimizing an arc setup. For this reason alone, no surgical or therapeutic activity and in particular, no surgical or therapeutic step is necessitated or implied by carrying out the invention.

Definitions

In this section, definitions for specific terminology used in this disclosure are offered which also form part of the present disclosure.
Computer Implemented Method The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Acquiring Data

The expression acquiring data like e.g. an arc setup for example encompasses (within the framework of a computer implemented method) the scenario in which the arc setup is determined by the computer implemented method or program. Determining data, i.e. an arc setup, for example encompasses measuring physical quantities and transforming the measured values into data, for example digital data, and/or computing (and e.g. outputting) the data by means of a computer and for example within the framework of the method in accordance with the invention. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Treatment Beam

The present invention relates to the field of controlling a treatment beam. The treatment beam treats body parts which are to be treated and which are referred to in the following as "treatment body parts". These body parts are for example parts of a patient's body, i.e. anatomical body parts.

The present invention relates to the field of medicine and for example to the use of beams, such as radiation beams, to treat parts of a patient's body, which are therefore also referred to as treatment beams. A treatment beam treats body parts which are to be treated and which are referred to in the following as "treatment body parts". These body parts are for example parts of a patient's body, i.e. anatomical body parts. Ionising radiation is for example used for the purpose of treatment. For example, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation include x-rays, high-energy particles (high-energy particle beams) and/or ionising radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumour are treated using ionising radiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

Reference is also made in this respect to the following web pages: http://www.elekta.com/healthcare_us_elekta_vmat.php and http://www.varian.com/us/oncology/treatments/treatment_techniques/rapidarc.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

In the following, a short description of the specific features of the present invention is given which shall not be understood to limit the invention only to the features or a combination of the features described in this section.

Figure 1:
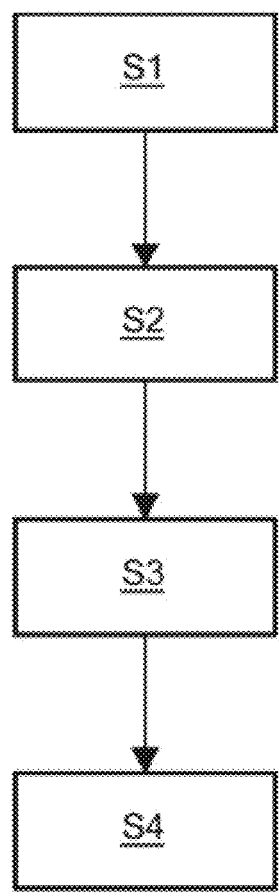
FIG. 1 illustrates a flow diagram of a computer-implemented medical method for radiation treatment (RT) planning for treating multiple brain metastases of a patient according to an exemplary embodiment.

FIG. 1 illustrates the basic steps of the method according to the first aspect, in which a first arc setup comprising a plurality of arcs is acquired in step S1, each arc being defined by a combination of a patient table angle, a gantry start angle and a gantry stop angle. Furthermore, the step of packing/distributing a plurality of target volumes, which describe the brain metastases, to the arcs of the first arc setup thereby providing a packed first arc setup is shown with step S2. Said first packed arc setup is compared with one or more predefined arc setup constraints in the step S3, wherein the predefined arc setup constraints comprise at least one of the following parameters: the number of patient table angles per target volume, the number of passes, the sum of gantry span per metastasis over all arcs, the minimum table span and the total number of patient table angles. More constraints may of course be comprised, as has been explained hereinbefore in great detail. And the method of FIG. 1 also comprises the step of automatically suggesting at least a second arc setup based on a result of the comparison, shown in step S4.

Several iterations of such a method can be carried out based on e.g. the comparison between an arc setup and the following, subsequent arc setup in the iteration. If this optimization is converging, which can be controlled by means of e.g. a predefined convergence criterion, this method of automatically finding an optimized arc setup may be stopped and the result may be further used in completely defining the radiotherapy treatment plan.

This method is a novel approach to automatically find an optimized arc setup for RT treatment planning. Such an automatically optimized arc setup can then be used in the existing and aforementioned software solutions to carry out the "core optimization" thereby optimizing the degrees of freedom 3-5, as elucidated hereinbefore, to find the optimal dose distribution. The inventors of the present invention have found that using such an automatically optimized arc setup generally leads to an improved RT treatment plan and corresponding medical results. It should be noted that the present invention can of course be applied not only to multiple brain metastases, but to any other multiple targets within a human body.

It will be explained in greater detail in the context of the following embodiment of FIG. 6 how such initial, i.e. a first, packed arc setup can be acquired. As becomes clear from this embodiment an initial, i.e. the first, packed arc setup is compared with the one or more predefined arc setup constraints. These predefined arc setup constraints at least constrain one of the number of patient table angles per target volume, the number of passes, the sum of gantry span per metastasis over all arcs, the minimum table span and the total number of patient table angle. Based on the result of the comparison between the first packed arc setup with said one or more predefined arc setup constraints a second arc setup is automatically suggested. The automatically suggested second arc setup may then be compared with the first one by calculating a score for both setups. Also the score calculation will be explained in more detail in the embodiment of FIG. 6. Said predefined constraints preferably define a respective minimum and a maximum value, as has been explained hereinbefore in detail.

As is clear to the skilled reader the presented method of FIG. 1 improves treatment efficiency and time by lowering the number of table angles and arcs for relatively easy geometries. It also improves treatment planning time by reducing the need for manual arc setup changes by the user and subsequent re-optimization of degrees of freedom 2-5. Moreover, the "core optimization" as described herein guarantees that the coverage is satisfied for each target volume. Therefore, it cannot be improved in principal. However, for an improved arc setup, as provided by the present invention, it is easier to sculp the prescription isodose around the shape of the target volume. We refer to this as target conformity. It also improves dose distribution in terms of limiting dose to risk structures by shortening arcs, closing projected shapes and adapting table angles to avoid irradiation through risk structures.

Figure 2:
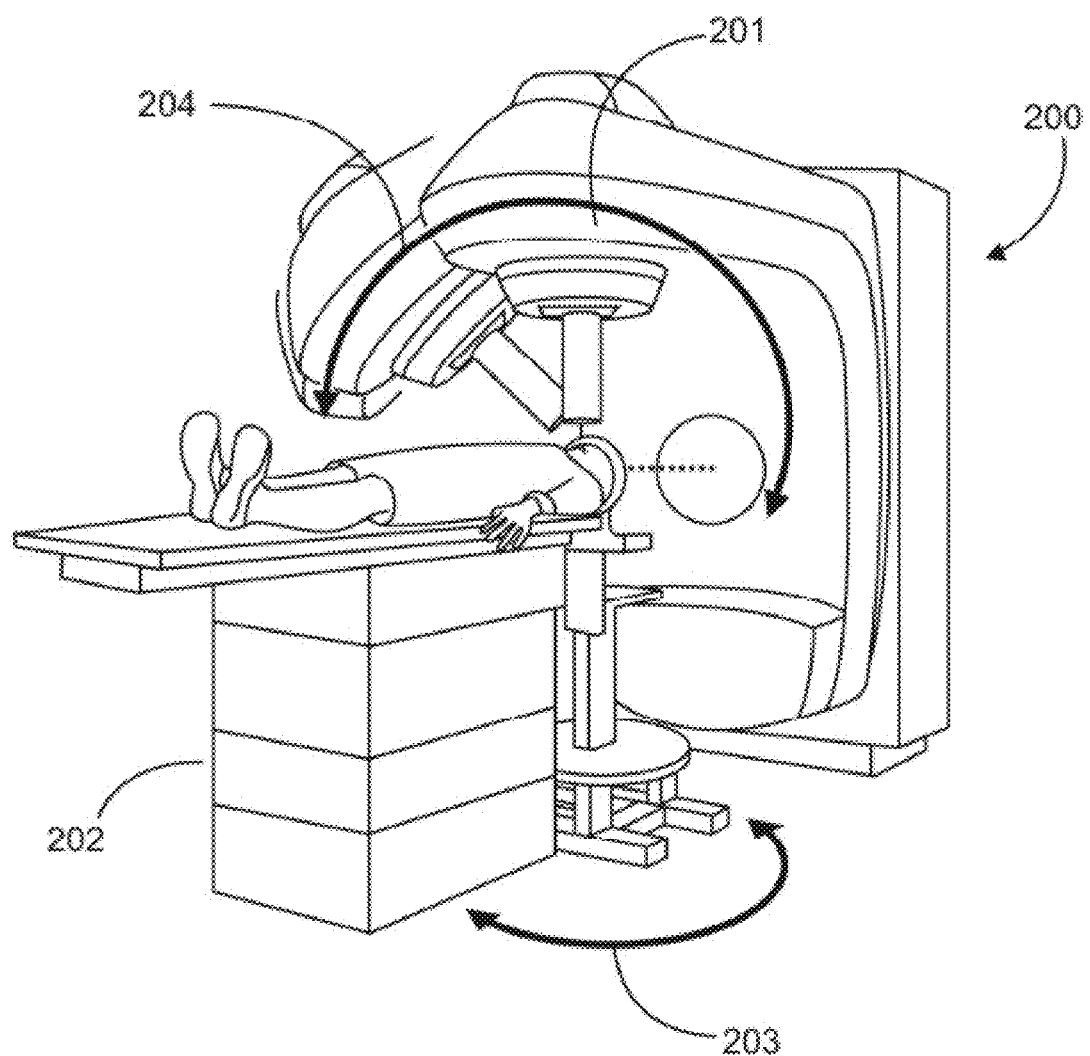
FIG. 2 schematically shows a radiation treatment (RT) apparatus according to an exemplary embodiment of the present invention.

FIG. 2 schematically shows a radiation treatment (RT) apparatus 200 according to an exemplary embodiment of the present invention. The RT apparatus 200 comprises a treatment beam source 201 and a patient support unit 202, which is embodied as a patient table 202. At least one computer is operably coupled to the RT apparatus for issuing a control signal to the radiation treatment apparatus for controlling, on the basis of an arc setup suggested according to e.g. the method described in the context of FIG. 1, 5 or 6, the operation of the treatment beam source 201 or the position of the patient support unit 202. In FIG. 2 the patient table angle is depicted by arrow 203 and the gantry angle is depicted by arrow 204.

Figure 3:
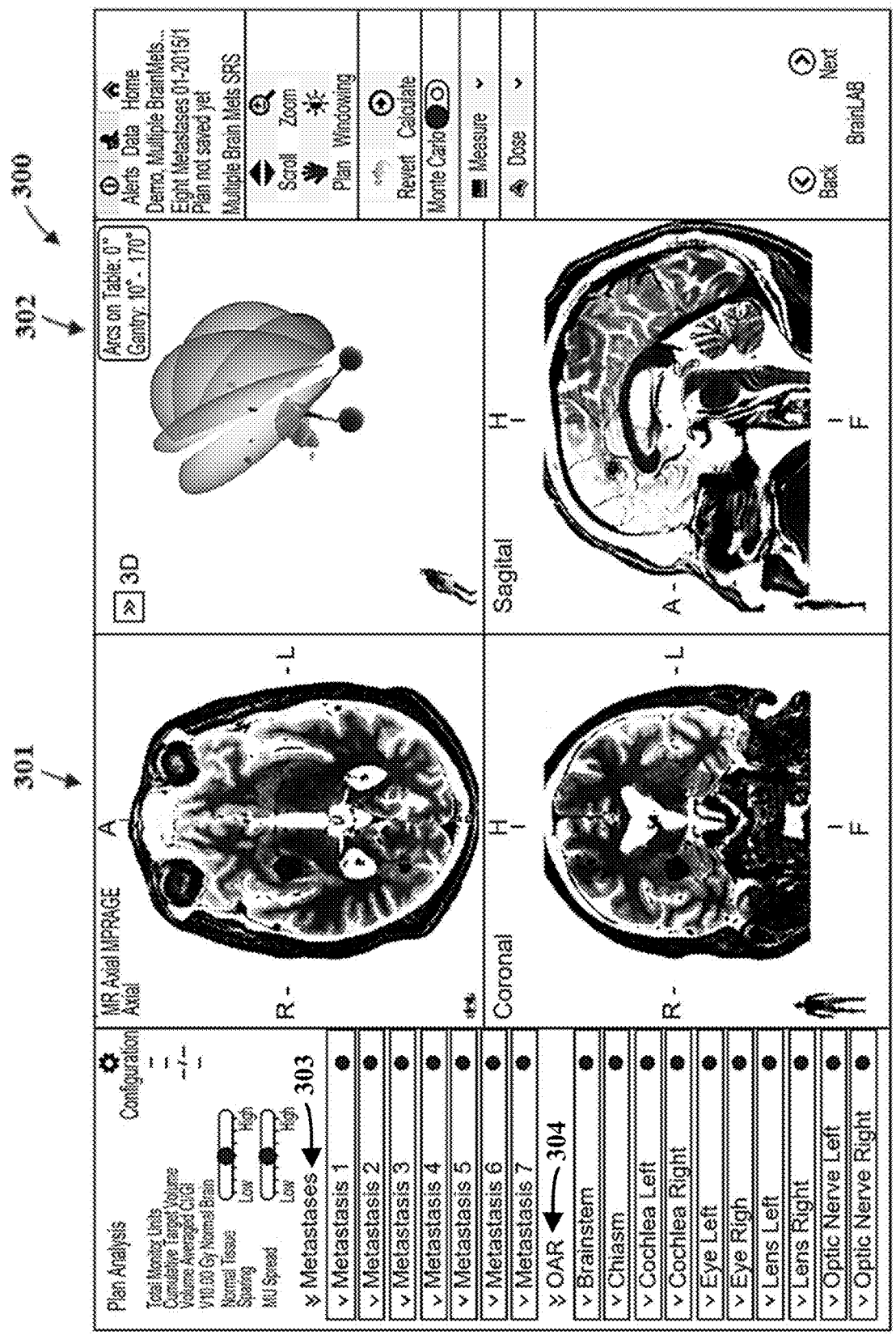
FIGS. 3 and 4 are schematic illustrations of user interfaces of a computer program according to an exemplary embodiment of the present invention.
Figure 4:
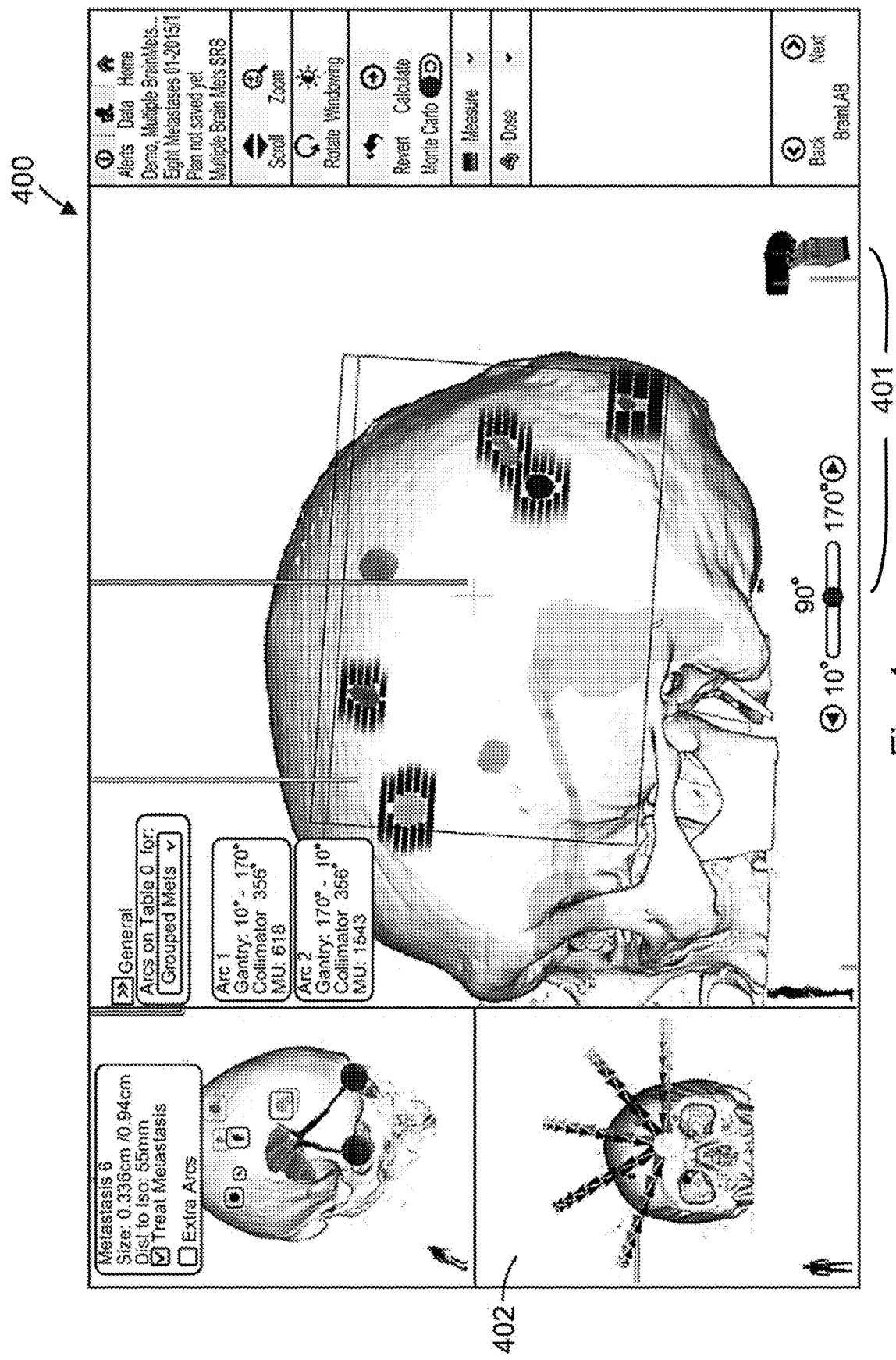

FIGS. 3 and 4 are both schematic illustrations of different user interfaces 300 and 400 of a computer program according to an exemplary embodiment of the present invention. In user interface 300 medical image data 301 are shown, which describe or define the metastases of a patient. Such data may be provided in digital form like e.g. in the form of MRI data. In such medical imaging data a contouring could be carried out thus specifically defining the metastasis for the practitioner and/or for the computer applying the method presented herein. User interface 300 further shows an arc set up that was suggested by using the method of the present invention. This arc setup comprises a plurality of arcs, each arc being defined by a combination of a patient table angle, a gantry start angle and a gantry stop angle. Also the different metastases that are irradiated during different arcs can be seen from 302. On the left hand side of user interface 300 tool bars 303 and 304 can be seen, on which the metastases can be individually selected 303. Also organ at risks (OAR) can be specified in tool bar 304.

User interface 400 of FIG. 4 shows for a specific gantry angle, which is illustrated by angle slide bar 401 and the corresponding depiction 401, the openings defined by the leaves of the collimator and the projected shapes of the metastases of an individual patient. The different arcs of the arc setup shown in FIG. 4 and the corresponding passes are shown in the left corner by picture 402. It can be seen that some metastases will be irradiated during this arc of the arc setup, whereas other metastasis will not be irradiated.

Figure 5:
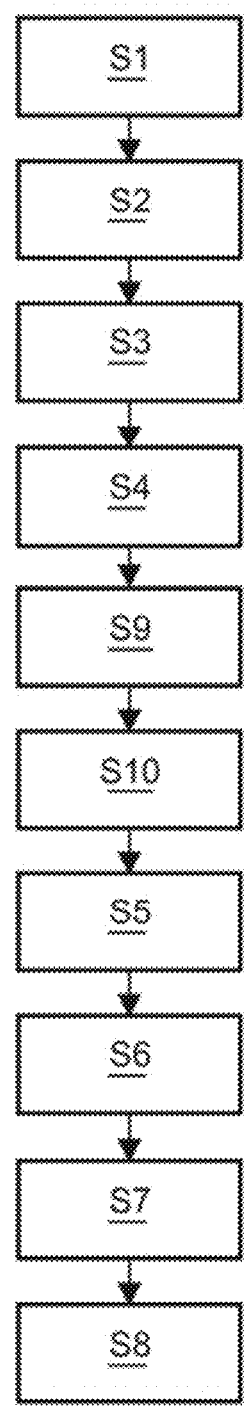
FIG. 5 illustrates a flow diagram of a computer-implemented medical method for radiation treatment (RT) planning for treating multiple brain metastases of a patient according to another exemplary embodiment of the present invention.

FIG. 5 illustrates a flow diagram of a computer-implemented medical method for radiation treatment (RT) planning for treating multiple brain metastases of a patient according to another exemplary embodiment of the present invention. For the steps S1 to S4 it is kindly referred to FIG. 1.

The method of FIG. 5 further comprises the step of removing a patient table angle and/or a pass from the first arc setup in step S9, if a result of the comparison of the first packed arc setup with the predefined arc setup constraints is that none of the constraints of
  a. the minimum number of patient table angles per target volume,
  b. the minimum number of times the gantry moves along one arc per patient table angle,
  c. the minimum sum of gantry span per metastasis over all arcs, and
  d. the minimum number of the total number of patient table angles are violated.

If this yields an arc setup with a decreased number of violated constraints, this new arc setup may be then used for further optimization e.g. using the present invention, or if it is decided that this shall be the final arc setup it may be used as RT plan for irradiating the metastases of the patient with an RT apparatus.

Moreover, the method of FIG. 5 further comprises the step of adding a patient table angle and/or a pass to the first arc setup in step S10, if a result of the comparison of the first packed arc setup with the predefined arc setup constraints is that none of the constraints of
  a. the maximum number of table angles per target volume,
  b. the maximum number of times the gantry moves along one arc per table angle,
  c. the maximum sum of gantry span, and
  d. the maximum number of the total number of patient table angles are violated.

If this yields an arc setup with a decreased number of violated constraints, this new arc setup may be then used for further optimization e.g. using the present invention, or if it is decided that this shall be the final arc setup it may be used as RT plan for irradiating the metastases of the patient with an RT apparatus The embodiment of FIG. 5 further comprises the steps of calculating a first score for the first packed arc setup in step S5, and distributing the plurality of target volumes, which describe the brain metastases, to the arcs of the suggested second arc setup thereby providing a packed second arc setup in step S6. Further, a second score for the packed second arc setup is calculated in step S7, and the first and second scores are compared in step S8. This aspect of calculating a score for the repacked new arc setups to compare them and/or to evaluate whether the score converges during several iterations of the presented method, can also be gathered from the details explained hereinbefore and also from the following embodiment of FIG. 6.

Figure 6:
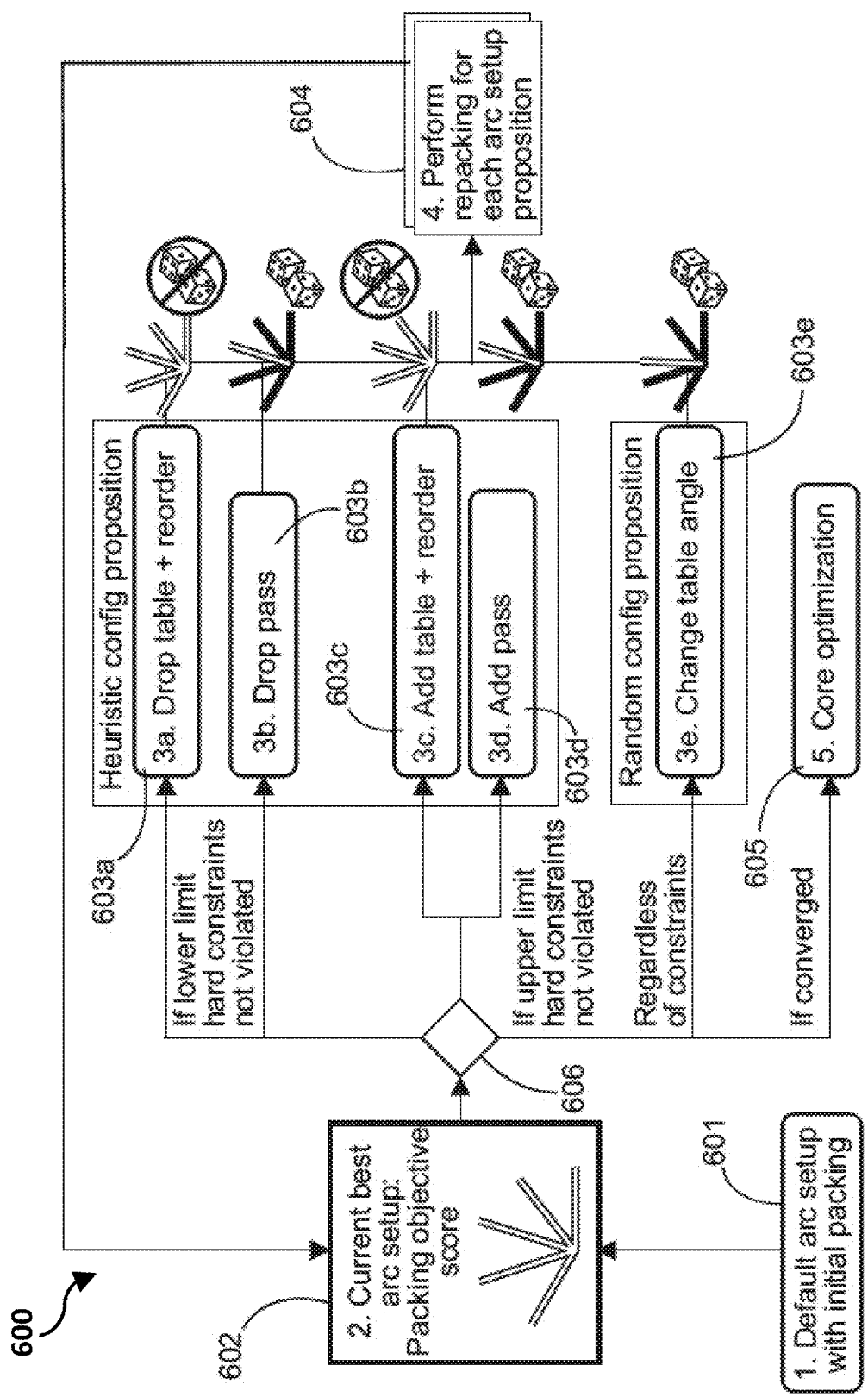
FIG. 6 illustrates another detailed embodiment of the computer-implemented medical method of the present invention.

FIG. 6 depicts an arc setup optimization loop, which realizes an exemplary embodiment of a computer-implemented medical method 600 for RT planning for treating multiple brain metastases of a patient. For the description of the following embodiment of FIG. 6 the following differentiation between three tissue types is used. A. Target volumes: the volumes of interest containing the brain metastases, which are selected for treatment by irradiation. B. Normal tissue: the volume of the patient's head surrounding the target. C. Risk structures: Predefined volumes of interest, typically corresponding to vital organs (e.g. brainstem, eye, optical nerve). The aim of treatment planning is to find an irradiation plan, which delivers the prescribed dose values to the target volumes, while minimizing the dose to surrounding normal tissue. Moreover, dose limits can be set for risk structures, to constrain dose to the respective localities. As will become apparent from the following explanation this embodiment of the present invention provides an improved arc setup as compared to prior art solutions.

The inventors of the present invention suggest that for dynamic conformal arc treatment plan optimization, several degrees of freedom are available:
1. Arc setup
2. Distribution of target volumes to arcs
3. Arc-weights (monitor units)
4. Opening or closing of a projected shape per control point
5. Margin per metastasis per arc The first part of the exemplary embodiment described in the context of FIG. 6 finds a suitable distribution of target volumes to arcs (i.e. "packing", degree of freedom 2) such that each metastasis is irradiated from as many different angles as possible. The second part of the algorithm (referred to as "core optimization") uses degrees of freedom 3-5 to find a dose distribution which is optimal in terms of sufficient dose to the target volumes (A), preventing dose to normal tissue (B) and limiting dose to risk structures (C).

Automatic Optimization of Arc Setups

The presented embodiment of FIG. 6 describes a novel approach to optimization of the arc setup (degree of freedom 1) to first improve treatment efficiency/time (by lowering the number of table angles/arcs for relatively easy geometries). Second treatment planning time is improved by reducing the need for manual arc setup changes by the user and subsequent re-optimization of degrees of freedom 2-5. Moreover, the dose distribution is improved in terms of target volume coverage (A) and normal tissue (B) by increasing the number of table angles/arcs for relatively complex geometries. Furthermore, the dose distribution is improved in terms of limiting dose to risk structures (C) by shortening arcs, closing projected shapes/adapting table angles to avoid irradiation through risk structures.

Definition of Hard Constraints

The arc setup optimization algorithm of FIG. 6 is based on a definition of hard constraints, which according to a preferred embodiment shall be fulfilled for each proposed arc setup:

The number of patient table angles, i.e. table angles, per target volume (e.g. minimum 3, maximum 4, too less table angles would result in worse target volume coverage/higher normal tissue dose, too many table angles would result in a long treatment time without substantial improvement in the dose distribution).

The total number of table angles (e.g. minimum 3, maximum 10, too less table angles would result in worse target volume coverage/higher normal tissue dose, too many table angles would result in a long treatment time without substantial improvement in the dose distribution).

The number of passes per table angle (e.g. minimum 1, maximum 4, using multiple passes may improve the packing (distribution of target volumes to arcs), which could be especially useful for clinics limiting the number of table angles).

Sum of gantry span per metastasis over all arcs (e.g. minimum 450, maximum 650, a large gantry span (when distributed over multiple table angles) may improve target volume coverage/normal tissue dose, a small gantry span per metastasis will result in more efficient deliveries).

Minimal table span (e.g. 90, makes sure that the optimization result remains stable and that target volumes are irradiated from a wide enough range of table positions).

The hard constraints may be either preset by the manufacturer based on retrospective treatment plan analysis or can be made user definable.

The method or algorithm 600 shown in FIG. 6 is initialized in step 601 with a default arc setup (based on e.g. experience with the released versions of the Multiple Brain Mets SRS software, consisting of e.g. a non-symmetric ensemble of five arc templates with two passes per template). An initial target volume to arcs distribution is established in step 601 by running the packing algorithm as is known to the skilled reader from existing solutions. In a second step 602, the initiation of the optimization loop (through steps 602, 603, 604) by evaluating the hard constraints on the initial or current best solution is carried out. In the third step, including steps 603a-603e, multiple new arc setups are suggested based on the result of step 602 and based on the comparison 606 with the one or more predefined arc setup constraints. This suggestion is done heuristically and stochastically as follows.

In steps 603a and 603b it is considered that if none of the lower limit hard constraints (as described before) are violated the algorithm proposes either dropping 603a a table angle (randomly or heuristically, with reordering of table angles) and/or dropping a pass (randomly or heuristically) 603b. If this yields an arc setup with a decreased number of violated constraints, this new arc setup may be then used for further optimization e.g. using the present invention, or if it is decided that this shall be the final arc setup it may be used as RT plan for irradiating the metastases of the patient with an RT apparatus. As is clear to the skilled reader in 602, if for a target volume a minimum constraint is not violated a removal of pass/table is generated in 603. However, the decision whether this actually results in an overall decreased number of violated constraints is done after performing step 604, as this performs a new packing and might change the whole distribution of target volumes to arcs. It must be noted that the feature "the predefined arc setup constraint about the number of patient table angles defines a minimum number of patient table angles" covers the parameter of "the number of patient table angles per target volume", and also covers additionally or alternatively (i.e. and/or) the parameter of the "total number of patient table angles".

The heuristics can be based on e.g. the number of metastases packed to an arc: passes and/or table angles with lowest number of packed target volumes and/or lowest total field size shall be removed first. In a particular embodiment of steps 603a and 603b, it is determined whether the predefined minimum of the number of patient table angles is violated by comparing the first packed arc setup with this minimum number. And if this is not the case then it is determined whether the removal of a patient table angle from the first packed arc setup will lead to a new packed arc setup, with which at least one violation of the one or more pre-defined arc setup constraints, that was present for the first/previous packed arc setup, can now be avoided. In this sense, such a removal of a patient table angle from the first/previous packed arc would lead to a new arc setup with a decreased number of violated constraints. The same principle applies and holds true of course for also the removal/drop of a pass in step 603b.

In steps 603c and 603d it is considered that if none of the upper limit hard constraints are violated the algorithm proposes either in 603c adding a table angle (randomly or heuristically, with reordering of table angles) or in 603d adding a pass (randomly or heuristically). If this yields an arc setup with an overall decreased number of violated constraints, this new arc setup may be then used for further optimization e.g. using the present invention, or if it is decided that this shall be the final arc setup it may be used as RT plan for irradiating the metastases of the patient with an RT apparatus. The heuristics can be based on e.g. the number of metastases packed to an arc: passes and/or table angles shall be added such that the number of packed target volumes and/or total field size shall be locally increased. Moreover, regardless of the hard constraints, the algorithm randomly proposes in step 603e the change of a table angle into a direction. In a particular embodiment of steps 603c and 603d, it is determined whether the pre-defined maximum of the number of patient table angles is violated by comparing the first packed arc setup with this maximum number. And if this is not the case then it is determined whether the addition of a patient table angle to the first packed arc setup will lead to a new packed arc setup, with which at least one violation of the one or more pre-defined arc setup constraints, that was present for the first/previous packed arc setup, can now be avoided. In this sense, such an addition of a patient table angle to the first/previous packed arc would lead to a new arc setup with a decreased number of violated constraints. The same principle as was just explained for the addition of a patient table angle applies and holds true of course for also the addition of a pass in step 603d.

If risk structures are to be considered, table angle changes are proposed/suggested such that radiating directly through such a structure can be avoided. This information can be obtained by analysis of the overlap of the projection of the risk structure and target volume to the arc. If it violates both upper and lower hard constraints, 603a-603d will not be performed, but 603e like in any case.

In the step 604 the packing algorithm is performed for each proposed arc setup. This results in new distributions of the target volumes over the various arcs. Each arc setup will be assigned a score value based on the packing objective function (explained below). The setup with optimal score will be chosen as current best arc setup, which is then used as input for step 602 in a next iteration. This describes the iterative method as was already explained in great detail hereinbefore for other embodiments. If the optimization converges, the best arc setup is used as input for the step 605, i.e. the core optimization. This step optimizes degrees of freedom 3-5 as defined before.

By way of the detailed explanation of this embodiment, it becomes clear that this method provides an improved arc setup as compared to arc setups used in the prior art RT treatment planning systems. The method 600 shown in FIG. 6 is a prime example of the computer-implemented medical method for radiation treatment (RT) planning for treating multiple brain metastases of a patient of the present invention. The method 600 comprising the steps of:

acquiring a first arc setup comprising a plurality of arcs, each arc being defined by a combination of a patient table angle, a gantry start angle and a gantry stop angle (601), distributing a plurality of target volumes, which describe the brain metastases, to the arcs of the first arc setup thereby providing a packed first arc setup (601), comparing said first packed arc setup with one or more predefined arc setup constraints (606), wherein the predefined arc setup constraints are selected from the following parameters: the number of patient table angles per target volume, the number of passes, the sum of gantry span per metastasis over all arcs, the minimum table span and the total number of patient table angle. And the method of the embodiment shown in FIG. 600 comprises the step of automatically suggesting at least a second arc setup based on a result of the comparison (603a-603e).

As is apparent from the above description, the method disclosed in FIG. 6 is carried out in several iterations based on the comparison between an arc setup and the following, subsequent arc setup in the iteration. If this optimization is converging, which can be controlled by means of e.g. a predefined convergence criterion, this method of automatically finding an optimized arc setup is stopped and the result may be further used for the core optimization and in completely defining the radiotherapy treatment plan.

The invention claimed is:

1. A computer-implemented method for radiation treatment (RT) planning for treating multiple brain metastases of a patient, the method comprising:

S1. receiving, from a data source or via an interface, a first arc setup comprising a plurality of arcs, each arc being defined by a combination of a patient table angle, a gantry start angle, and a gantry stop angle;

S2. distributing a plurality of target volumes, which describe the multiple brain metastases, to the plurality of arcs of the first arc setup thereby providing a packed first arc setup;

S3. comparing the packed first arc setup with one or more predefined arc setup constraints, wherein the one or more predefined arc setup constraints are selected from: a number of patient table angles per target volume, a number of passes with each pass being defined by a patient table angle, a gantry start angle, a gantry stop angle and a set of target volumes, a number of times a gantry moves along one arc per patient table angle, a sum of gantry span per target volume over all arcs, a minimum table span, and a total number of patient table angles in the packed first arc setup; and S4. automatically suggesting at least a second arc setup based on a result of comparing the packed first arc setup with the one or more predefined arc setup constraints, wherein the method comprises any one or both of (i) and (ii), wherein:

(i) the number of patient table angles per target volume defines a minimum number of patient table angles per target volume, wherein, if a result of comparing the packed first arc setup with the one or more predefined arc setup constraints is that the minimum number of patient table angles per target volume is not violated, the method comprises:

removing a patient table angle from the first arc setup; and (ii) the number of passes defines a minimum number of passes, and wherein, if the result of comparing the packed first arc setup with the one or more predefined arc setup constraints is that the minimum number of passes is not violated, the method comprises:

removing a pass from the first arc setup.

2. The method according to claim 1, wherein a minimum and a maximum are defined for each of the one or more predefined arc setup constraints.

3. The method according to claim 1, wherein removing the patient table angle, or the pass, or the patient table angle and the pass from the first arc setup is based on a number of target volumes packed to an arc, and wherein removing the patient table angle, or the pass, or the patient table angle and the pass from the first arc setup comprises first removing at least one of the patient table angles or passes with a lowest number of packed target volumes.

4. The method according to claim 1, further comprising:
randomly selecting at least one pass of the first arc setup to be removed from the first arc setup.

5. The method according to claim 1, further comprising:
reordering, after removing said patient table angle, the remaining patient table angles of the second arc setup.

6. The method according to claim 1, wherein the method comprises any one or both of (i) and (ii), wherein:
(i) the number of patient table angles per target volume defines a maximum number of patient table angles per target volume, wherein, if a result of comparing the packed first arc setup with the one or more predefined arc setup constraints is that the maximum number of patient table angles per target volume is not violated, the method comprises:
adding a patient table angle to the first arc setup; and
(ii) the number of passes defines a maximum number of passes, and wherein, if the result of comparing the packed first arc setup with the one or more predefined arc setup constraints is that the maximum number of passes is not violated, the method comprises:
adding a pass to the first arc setup.

7. The method according to claim 6, wherein adding the patient table angle, or the pass, or the patient table angle and the pass to the first arc setup is based on a number of target volumes packed to an arc, and wherein adding the patient table angle, or the pass, or the patient table angle and the pass to the first arc setup comprises increasing the number of target volumes packed to an arc.

8. The method according to claim 6, further comprising:
reordering patient table angles of the second arc setup with the added patient table angle.

9. The method according to claim 1, wherein in S4, the automatically suggesting at least the second arc setup comprises automatically suggesting a plurality of arc setups based on the result of comparing the packed first arc setup with the one or more predefined arc setup constraints, wherein for:
a first arc setup of the plurality of suggested arc setups, a patient table angle is removed from the first arc setup;
a second arc setup of the plurality of suggested arc setups, a pass is removed from the first arc setup;
a third arc setup of the plurality of suggested arc setups, a patient table angle is added to the first arc setup;
a fourth arc setup of the plurality of suggested arc setups, a pass is added to the first arc setup; and
a fifth arc setup of the plurality of suggested arc setups, a random change of at least one patient table angle of the first arc setup is caused.

10. The method according to claim 1, wherein the one or more predefined arc setup constraints comprises:
the number of patient table angles per target volume which defines a minimum and a maximum number of patient table angles per target volume;
the number of times the gantry moves along one arc per patient table angle which defines a minimum and a maximum number of times the gantry moves along one arc per patient table angle;
the sum of gantry span per target volume over all arcs which defines a minimum and a maximum sum of gantry span per target volume over all arcs; and
the total number of patient table angles which defines a minimum and a maximum number of the total number of patient table angles.

11. The method according to claim 10, wherein, if a result of comparing the packed first arc setup with the one or more predefined arc setup constraints is that none of the one or more predefined arc setup constraints are violated, where the one or more predefined arc setup constraints consists of:
the minimum number of patient table angles per target volume,
the minimum number of times the gantry moves along one arc per patient table angle,
the minimum sum of gantry span per metastasis over all arcs,
the minimum number of the total number of patient table angles, and
the minimum and a maximum number of the total number of patient table angles,
the method further comprises:
removing a patient table angle, or a pass, or a patient table angle and a pass from the first arc setup.

12. The method according to claim 11, wherein removing the patient table angle, or the pass, or the patient table angle and the pass from the first arc setup is based on a number of target volumes packed to an arc, and wherein removing the patient table angle, or the pass, or the patient table angle and the pass from the first arc setup comprises first removing at least one of the patient table angles or passes with a lowest number of packed target volumes.

13. The method according to claim 11, further comprising:
randomly selecting at least one pass of the first arc setup to be removed from the first arc setup.

14. The method according to claim 10, wherein, if a result of comparing the packed first arc setup with the one or more predefined arc setup constraints is that none of the one or more predefined arc setup constraints are violated, where the one or more predefined arc setup constraints consists of:
the maximum number of patient table angles per target volume,
the maximum number of times the gantry moves along one arc per patient table angle,
the maximum sum of gantry span per metastasis over all arcs, and
the maximum number of the total number of patient table angles,
the method further comprises:
adding a patient table angle, or a pass, or a patient table angle and a pass to the first arc setup.

15. The method according to claim 14, wherein adding the patient table angle, or the pass, or the patient table angle and the pass to the first arc setup is based on a number of target volumes packed to an arc, and wherein adding the patient table angle, or the pass, or the patient table angle and the pass to the first arc setup comprises increasing the number of target volumes packed to an arc.

16. The method according to claim 15, further comprising:
reordering the patient table angles of the second arc setup with the added patient table angle.

17. The method according to claim 1, further comprising:
S5. calculating a first score for the packed first arc setup;
S6. distributing the plurality of target volumes, which describe the brain metastases, to the arcs of the suggested second arc setup thereby providing a packed second arc setup;
S7. calculating a second score for the packed second arc setup; and
S8. comparing the first and second scores.

18. The method according to claim 17, further comprising:
repeating S1 to S8 in a plurality of iterations until a calculated score for a packed final arc setup of a final arc setup, which was automatically suggested during a final iteration of the plurality of iterations, fulfils a predefined convergence criterion.

19. The method according to claim 18, wherein for the final arc setup, the method further comprising:
for the final arc setup, optimizing at least one of the following parameters:
arc-weight for each arc of the final arc setup, wherein the arc-weight is a measure of energy applied by a radiation treatment apparatus during a particular arc,
positions of leaves of a multi-leaf collimator of the radiation treatment apparatus, and
a positive or negative margin per target volume and per arc.

20. The method according to claim 18, further comprising:
for the final arc setup, optimizing at least one of the following parameters:
arc-weight for each arc of the final arc setup, wherein the arc-weight is a measure of energy applied by a radiation treatment apparatus during a particular arc,
positions of leaves of a multi-leaf collimator of the radiation treatment apparatus, and
a positive or negative margin per target volume and per arc; and
transferring the final arc setup or a result of the optimization of the at least one of the parameters of the final arc setup to the radiation treatment apparatus for irradiating the metastases of the patient.

21. The method according to claim 1, wherein in S4, the automatically suggesting at least the second arc setup comprises automatically suggesting a plurality of arc setups and further wherein the automatically suggesting comprises a heuristically derived suggestion for at least one arc setup of the plurality of arc setups and comprises a stochastically derived suggestion for at least one arc setup of the plurality of arc setups.

22. The method according to claim 1, further comprising:
generating a random change of a patient table angle of the first arc setup for the suggested second arc setup.

23. The method according to claim 22, wherein generating the random change of the patient table angle takes into account predefined risk structures of the patient.

24. A non-transitory computer readable storage medium storing a program comprising program instructions, that when executed on at least one processor of a computer or loaded onto the at least one processor of the computer, causes the computer to perform a method for radiation treatment (RT) planning for treating multiple brain metastases of a patient by:
receiving, from a data source or via an interface, a first arc setup comprising a plurality of arcs, each arc being defined by a combination of a patient table angle, a gantry start angle, and a gantry stop angle;
distributing a plurality of target volumes, which describe the multiple brain metastases, to the plurality of arcs of the first arc setup thereby providing a packed first arc setup;
comparing the packed first arc setup with one or more predefined arc setup constraints, wherein the one or more predefined arc setup constraints are selected from: a number of patient table angles per target volume, a number of passes with each pass being defined by a patient table angle, a gantry start angle, a gantry stop angle and a set of target volumes, a number of times a gantry moves along one arc per patient table angle, a sum of gantry span per target volume over all arcs, a minimum table span, and a total number of patient table angles in the packed first arc setup; and
automatically suggesting at least a second arc setup based on a result of comparing the packed first arc setup with the one or more predefined arc setup constraints,
wherein the method comprises any one or both of (i) and (ii), wherein:
(i) the number of patient table angles per target volume defines a minimum number of patient table angles per target volume, wherein, if a result of comparing the packed first arc setup with the one or more predefined arc setup constraints is that the minimum number of patient table angles per target volume is not violated, the program comprising the program instructions further causes the computer to perform the method by:
removing a patient table angle from the first arc setup; and
(ii) the number of passes defines a minimum number of passes, and wherein, if the result of comparing the packed first arc setup with the one or more predefined arc setup constraints is that the minimum number of passes is not violated, the program comprising the program instructions further causes the computer to perform the method by:
removing a pass from the first arc setup.

25. A medical system, comprising:
at least one computer;
at least one electronic data storage device storing at least patient data describing multiple brain metastases of a patient; and
a medical device for carrying out a medical procedure on the patient,
wherein the at least one computer is operable to:
receive, from a data source or via an interface, a first arc setup comprising a plurality of arcs, each arc being defined by a combination of a patient table angle, a gantry start angle, and a gantry stop angle;
distribute a plurality of target volumes, which describe the multiple brain metastases, to the plurality of arcs of the first arc setup thereby providing a packed first arc setup;
compare the packed first arc setup with one or more predefined arc setup constraints, wherein the one or more predefined arc setup constraints are selected from: a number of patient table angles per target volume, a number of passes with each pass being defined by a patient table angle, a gantry start angle, a gantry stop angle and a set of target volumes, a number of times a gantry moves along one arc per patient table angle, a sum of gantry span per target volume over all arcs, a minimum table span, and a total number of patient table angles in the packed first arc setup; and automatically suggest at least a second arc setup based on a result of comparing the packed first arc setup with the one or more predefined arc setup constraints, wherein the at least one computer is operable to perform any one or both of (i) and (ii), wherein:
  (i) the number of patient table angles per target volume defines a minimum number of patient table angles per target volume, wherein, if a result of comparing the packed first arc setup with the one or more predefined arc setup constraints is that the minimum number of patient table angles per target volume is not violated, the at least one computer is operable to:
    remove a patient table angle from the first arc setup; and
  (ii) the number of passes defines a minimum number of passes, and wherein, if the result of comparing the packed first arc setup with the one or more predefined arc setup constraints is that the minimum number of passes is not violated, the at least one computer is operable to:
    remove a pass from the first arc setup, and
  wherein the at least one computer is operable to issue a control signal to the medical device for controlling operation of the medical device based on at least the second arc setup.

26. The medical system according to claim 25, wherein the medical device comprises:
  a radiation treatment (RT) apparatus comprising a treatment beam source and a patient support unit with a patient table,
  wherein the at least one computer is operably coupled to the radiation treatment apparatus for issuing a control signal to the radiation treatment apparatus for controlling, based on at least the second arc setup, at least one of an operation of the treatment beam source or a position of the patient support unit.

* * * * *